US011413304B2

United States Patent
Bellman et al.

(10) Patent No.: US 11,413,304 B2
(45) Date of Patent: Aug. 16, 2022

(54) STORAGE-STABLE OPHTHALMIC COMPOSITION

(71) Applicant: DR. GERHARD MANN CHEM.-PHARM. FABRIK GMBH, Berlin (DE)

(72) Inventors: Günther Bellman, Berlin (DE); Lutz Kröhne, Berlin (DE)

(73) Assignee: DR. GERHARD MANN CHEM.-PHARM. FABRIK GMBH, Berlin (DE)

(*) Notice: Subject to any disclaimer, the term of this patent is extended or adjusted under 35 U.S.C. 154(b) by 5 days.

(21) Appl. No.: 16/089,715

(22) PCT Filed: Apr. 12, 2017

(86) PCT No.: PCT/EP2017/058825
§ 371 (c)(1),
(2) Date: Sep. 28, 2018

(87) PCT Pub. No.: WO2017/178544
PCT Pub. Date: Oct. 19, 2017

(65) Prior Publication Data
US 2019/0111075 A1 Apr. 18, 2019

(30) Foreign Application Priority Data
Apr. 15, 2016 (EP) .................................. 16165546

(51) Int. Cl.
*A61K 31/728* (2006.01)
*A61K 47/14* (2017.01)
*A61K 47/32* (2006.01)
*A61K 47/36* (2006.01)
*A61K 9/00* (2006.01)
*A61K 9/08* (2006.01)
*A61P 27/02* (2006.01)
*A61K 47/10* (2017.01)
*A61K 47/26* (2006.01)

(52) U.S. Cl.
CPC .......... *A61K 31/728* (2013.01); *A61K 9/0048* (2013.01); *A61K 9/08* (2013.01); *A61K 47/10* (2013.01); *A61K 47/14* (2013.01); *A61K 47/26* (2013.01); *A61K 47/32* (2013.01); *A61K 47/36* (2013.01); *A61P 27/02* (2018.01)

(58) Field of Classification Search
None
See application file for complete search history.

(56) References Cited

U.S. PATENT DOCUMENTS

| 5,814,660 A * | 9/1998 | Selliah ............... A61K 31/5585 514/461 |
| 6,610,318 B1 * | 8/2003 | Bellmann ............... A61K 31/78 424/427 |
| 2006/0029571 A1 * | 2/2006 | Karageozian .......... A61P 27/02 424/78.38 |
| 2013/0210912 A1 * | 8/2013 | Davio .................. A61K 9/0048 514/530 |
| 2015/0025020 A1 * | 1/2015 | Garrigue ............... A61K 33/22 514/20.5 |

FOREIGN PATENT DOCUMENTS

| CA | 2616531 A1 * | 2/2007 | ............. A61K 47/32 |
| DE | 102012221224 A1 * | 5/2014 | ........... A61Q 19/005 |
| DE | 102014202377 A1 * | 8/2015 | ............. A61Q 17/04 |
| EP | 1913934 A1 * | 4/2008 | ............. A61K 36/52 |
| EP | 2221045 A1 * | 8/2010 | ........... A61K 8/8182 |

OTHER PUBLICATIONS

Aragona et al., Long term treatment with sodium hyaluronate-containing artificial tears reduces ocular surface damage in patients with dry eye, Br J Ophthalmol. Feb. 2002;86(2):181-4, printed from https://www.ncbi.nlm.nih.gov/pubmed/11815344, Abstract only, 2 pages.*
Aragona et al., Long term treatment with sodium hyaluronate-containing artificial tears reduces ocular surface damage in patients with dry eye, Br J Ophthalmol. Feb. 2002; 86(2): 181-184.*
Vereshchagin et al., The triglyceride composition of linseed oil, J Am Oil Chem Soc, Nov. 1965;42(11):970-4, printed from https://link.springer.com/article/10.1007/BF02632457, 7 pages, abstract only.*
De Greyt et al., Polymeric and oxidized triglyceride content of crude and refined vegetable oils—An overview, FETT-LIPID, 1997, 99 (8). p. 287-290, printed from https://onlinelibrary.wiley.com/doi/pdf/10.1002/lipi.19970990806, 8 pages.*
Mastromarino et al., The Effect of Medium Chain Triglycerides-Containing Tear Substitute on the Dynamics of Lipid Layer Interference Patterns (DLIP) in Dry Eye Patients, Investigative Ophthalmology & Visual Science May 2005, vol. 46, 2043, printed from https://iovs.arvojournals.org/article.aspx?articleid=2401522,.*
Rowe et al., Sodium Hyaluronate, Handbook of Pharmaceutical Excipients, 2009, Sixth Edition, Pharmacuetical Press, p. 646-648.*
International Preliminary Report on Patentability dated Oct. 16, 2018, issued in International Application No. PCT/EP2017/058825.
Marjorie J. Rah, "A Review of hyaluronan and its ophthalmic applications," Optometry, 2011, pp. 38-43, vol. 82.

* cited by examiner

*Primary Examiner* — Gigi G Huang
(74) *Attorney, Agent, or Firm* — Ryan, Mason & Lewis, LLP

(57) ABSTRACT

The present invention relates to a drop-forming, storage stable, multiphase, ophthalmic composition comprising at least one liquid aqueous phase and at least one liquid hydrophobic phase, characterized in that it is emulsifier-free as well as buffer-free and comprises hyaluronic acid and/or hyaluronate.

20 Claims, No Drawings

STORAGE-STABLE OPHTHALMIC COMPOSITION

This application claims priority under 35 U.S.C. § 371 to International Application No. PCT/EP2017/058825, filed Apr. 12, 2017 which claims the benefit of EP16165546.9 filed Apr. 15, 2016, and entitled "STORAGE-STABLE OPHTHALMIC COMPOSITION", the contents of which are incorporated herein by reference.

The present invention relates to a drop-forming, storage stable, ophthalmic composition as well as to its preparation and application.

It is commonly known, that eyes frequently burn, itch or tear in consequence of, e.g. intensive screen handling, wearing of contact lenses or dry room air caused by air conditioning. The reason for this is often a functional disorder of the tear film caused by an increased evaporation or too little tear production. However, a wetting defect of the eye can also be promoted by hormonal adjustment in old age, intake of medicines or internal diseases such as the Sjögren syndrome, rheumatism or diabetes.

It is known in the prior art to treat irritated or inflamed eyes, especially in the case of "dry eyes", keratokonjunktivitis sicca, with aqueous preparations. These preparations are usually available in form of fluids, gels or creams.

It is disadvantageous that ingredients are often added to solutions which lead to allergic reactions, irritations or intolerance towards the specific ingredients. Likewise, it is known from aqueous solutions that they frequently cause itching, burning or other unpleasant side effects when contacted with the eye. Moreover, especially preparations in form of gels, creams or ointments have the disadvantage that the application is perceived as additionally unpleasant by patients that already suffer from painful irritation of the eyes. In addition, the distribution of preparations in or at the eye has to be supported frequently by rubbing. A process that equally leads to an additional sensation of pain for the patient.

Two-phase emulsions are also known in the prior art. However, their stability inter alia depends on their viscosity. Accordingly, emulsions turn instable if, for instance, a hydrophobic phase that is finely dispersed in a hydrophilic phase aggregates. This process significantly limits the stability upon storage of the emulsion and proceeds the slower, the more viscous the continuous phase of the emulsion is. To reach sufficient stability of emulsions, emulsifiers are usually employed. However, emulsifiers might similarly lead to allergic or other reactions related to hypersensitivity.

An emulsifier-free preparation is, for example, disclosed in EP 1 913 934 A1. However, a disadvantage of this preparation is, that it exhibits a high viscosity. Thus, the application can be unpleasant for the patient and the distribution of the preparation, for instance, by rubbing in the eye can cause additional pain. Furthermore, the administration of highly viscous preparations from containers or single-dose containers is complicated, especially for older patients or patients with limited motoric abilities.

WO 2007/012625 A1 discloses a sterile, drop-forming, multiphase, emulsifier-free, ophthalmic preparation with a viscosity in the range from greater than or equal to 200 mPa·s and less than 2000 mPa·s. However, phosphate salts are used for these formulations. In rare cases of patients with significant corneal damage, these salts can react with the calcium present in the corneal stroma, which may cause aggregation of calcium phosphate (see BfArM & PEI Bulletin zur Arzneimittelsicherheit 2013, 1, 7-12).

Storage stable, multiphase, ophthalmic compositions are also disclosed in WO 2013/122801 A1. However, these compositions may contain emulsifiers, buffers or phosphate salts.

Therefore, there is still a need in the art for storage stable, ophthalmic compositions that are well-tolerable and avoid the known disadvantages.

Accordingly, it is an object of the present invention to provide an ophthalmic composition that is storage stable and well-tolerable. It is desirable that the composition is drop-forming and comprises a lipophilic component. Furthermore, it is desirable that the composition is storage stable also at low viscosity without the addition of emulsifiers or buffer substances.

Moreover, it is an object of the present invention to provide an ophthalmic composition for use as a medicament. It is desirable that the composition is suitable for treating diseases or conditions of the eye, or the organs or tissues surrounding the eye, or being connected herewith, and preferably for treating dry eye.

The above-mentioned and further objects are solved according to the subject-matter as defined in the independent claims.

According to one aspect of the present invention a storage stable, multiphase, ophthalmic composition is provided comprising at least one liquid aqueous phase and at least one liquid hydrophobic phase, characterized in that
 the composition is emulsifier-free,
 the composition is buffer-free, and
 the composition comprises hyaluronic acid and/or hyaluronate.

According to a further aspect of the present invention, a process for the preparation of a drop-forming, storage stable, multiphase, ophthalmic composition according to the present invention is provided, characterized in that a liquid hydrophobic phase is dispersed homogenously in a continuous liquid aqueous phase, wherein the liquid aqueous phase comprises hyaluronic acid and/or hyaluronate.

According to a further aspect of the present invention, a drop-forming, storage stable, multiphase, ophthalmic composition according to the present invention, is provided for use as a medicament.

According to a further aspect of the present invention, a drop-forming, storage stable, multiphase ophthalmic composition according to the present invention, is provided for use in treating diseases or conditions of the eye, or the organs or tissues surrounding the eye or being connected therewith and preferably for use in treating dry eye.

According to a further aspect of the present invention, a container comprising the composition according to the present invention is provided, where the container is a single-dose container or a multi-dose container, preferably an ophtiole, a single-dose ophtiole or an application system, preferably a pump-based application system or a tip-seal application system.

According to a further aspect of the present invention, the use of hyaluronic acid and/or hyaluronate for stabilization of a multiphase, emulsifier-free composition comprising at least one liquid aqueous phase and at least one liquid hydrophobic phase is provided.

Further preferred embodiments are described in the corresponding sub-claims.

In one embodiment, the composition exhibits a viscosity of less than 350 mPa·s at 20° C., preferably less than 250 mPa·s at 20° C. more preferably less than 200 mPa·s at 20° C., and even more preferably less 150 mPa·s at 20° C., and most preferably less than 100 mPa·s at 20° C. In another embodiment, the composition comprises hyaluronic acid and/or hyaluronate in an amount of at least 0.001 wt. %, based on the total weight of the composition, preferably in an amount of at least 0.01 wt. %, more preferably in an amount of at least 0.1 wt. %, even more preferably in an amount of at least 0.15 wt. % and most preferably in an amount of at least 0.2 wt. %.

In one embodiment, the hyaluronic acid and/or hyaluronate exhibits a molecular weight $M_w$ of from 50 000 to 10 000 000 g/mol, more preferably from 100 000 to 5 000 000 g/mol, and most preferably from 250 000 to 1 000 000 g/mol. In a further embodiment, the hyaluronate is selected from the group consisting of sodium hyaluronate, potassium hyaluronate, zinc hyaluronate, and mixtures thereof, preferably the hyaluronate is sodium hyaluronate. In a further embodiment, the composition comprises the liquid aqueous phase as continuous phase and the liquid hydrophobic phase as droplets dispersed therein.

In one embodiment, the composition comprises at least one polymeric, gel-forming component, preferably at least one polyacrylic acid and/or at least one polymeric acrylic acid derivative, and most preferably at least one carbomer. In a further embodiment, the liquid hydrophobic phase comprises an ophthalmic acceptable oil, preferably a triglyceride, and most preferably a medium-chain triglyceride. In another embodiment, the composition comprises an agent to adjust the isotonicity, preferably selected from the group consisting of dextrose, glycerin, propylene glycol, sorbitol, mannitol, urea, polyethylene glycol, boric acid, magnesium sulfate, zinc sulfate, sodium chloride, potassium chloride, calcium chloride, sodium sulfate, sodium hydrogen phosphate, trisodium citrate, trisodium phosphate, and mixtures thereof, more preferably selected from the group consisting of dextrose, glycerin, propylene glycol, sorbitol, mannitol, urea, polyethylene glycol, and most preferably glycerin.

In one embodiment, the composition comprises the following substances, based on the total weight of the composition:
   0.15 to 0.3 wt. % sodium hyaluronate,
   0.15 to 0.25 wt. % medium-chain triglyceride,
   0.05 to 0.1 wt. % carbomer.
   1.5 to 7 wt. % agents to adjust the isotonicity, preferably glycerin,
   sodium hydroxide for pH adjustment, and
   q.s. ad 100 wt. % water.

In one embodiment, the composition is in form of an eye lid spray, an eye bath, an eye wash solution, or eye drops, preferably in form of an eye lid spray or eye drops.

In the following, terms that are used in the present invention are explained:

For the purpose of the present invention, the term "drop-forming" means that the ophthalmic composition is able to form drops and therefore is applicable in the form of drops. The size of the drop depends on the container and especially the dropper, from which the composition is applied. For example, the drop size may be in a range of from 5 to 70 μL.

For the purpose of the present invention, the term "storage stable" means that no visible phase separation occurs and that the composition shows almost no or only slight variations with respect to pH value, osmolality, viscosity and appearance, when stored over a period of at least 12 months at a temperature from 2 to 8° C. In one embodiment, a composition is storage stable, if a drop, preferably 50 μL, of the composition shows, after being stored over a period of 12 months, a maximum of 10 oil droplets (lipophilic phase) with a droplet diameter of more than 150 μm and a maximum of 15 oil droplets (lipophilic phase) with a diameter of more than 100 μm. The droplet diameter of the lipophilic phase can be evaluated by microscopy.

For the purpose of the present invention, the term "emulsifier-free" means that the composition contains only ingredients, that are no emulsifiers within the meaning of the present invention. For the purpose of the present invention, "emulsifiers" are interface-active substances that are able to decrease the interfacial tension between the oil and the water phase by accumulating at the interface between these two phases. This is enabled by the amphiphilic molecular structure of the emulsifiers, which possesses at least one polar (hydrophilic) group and at least one unpolar (lipophilic) group. By this they are soluble in the hydrophilic and the lipophilic phase. The part which is more soluble in the corresponding phase extends into said phase and thereby decreases the interfacial tensions between both phases.

According to the present invention, the composition particularly can comprise substances selected from the group consisting of an ophthalmic acceptable oil, a polymeric, gel-forming component, an agent to adjust the isotonicity, an ophthalmic active ingredient, acids or bases to adjust the pH value, water and mixtures thereof, whereby these substances are no emulsifiers in the meaning of the present invention.

For the purpose of the present invention, the term "buffer-free" means that the composition comprises exclusively ingredients that are no buffers in the meaning the present invention. For the purpose of the present invention, a "buffer" may be a buffer system, e.g. a mixture of an acid and its conjugated base, or a buffer substance. Examples for buffers with the meaning of the present invention are phosphate buffers, phosphate citrate buffers, citrate buffers, tartrate buffers, borate buffers, malate buffers, succinate buffers, acetate buffers, acetate borate buffers, MES (2-(N-morpholino)ethanesulfonic acid), HEPES (2-(4-(2-hydroxyethyl)1-piperazinyl-ethanesulfonic acid), BES (N,N-bis(2-hydroxyethyl)-2-aminoethanesulfonic acid), MOPS (3-(N-morpholino)propanesulfonic acid), TRIS (tris(hydroxymethyl)aminomethane), or BIS-TRIS (bis(2-hydroxyethyl)amino-tris(hydroxymethyl)methane.

In one embodiment, the composition is buffer-free, if the buffer capacity $P_i$ of the composition is less than 0.005, and preferably less than 0.0005. To determine the buffer capacity $P_i$, a 0.1 N solution of sodium hydroxide is added to 10 mL of the composition to be tested until a pH change of 0.3 units occurs. The buffer capacity $P_i$ can then be determined as follows:

$$P_i = \frac{\text{mL alkaline solution} \cdot 0.1}{\text{pH change} \cdot 10}$$

(cf. Dolder, Skinner, Ophthalmika, 4. Volume, Wissenschaftliche Verlagsgesellschaft, page 606, chapter 4.1.2.4).

The term "viscosity" is understood herein, unless noted otherwise, as the dynamic viscosity, which is also known as the absolute viscosity. According to the present invention, the viscosity is determined by the Wells-Brookfield cone and plate procedure with a Wells-Brookfield cone and plate viscometer of the type DV-III+ (Brookfield Engineering Laboratories GmbH, Germany) equipped with a CP51 spindle at 5 rpm and 20° C. The viscosity refers, unless noted otherwise, to the viscosity of the composition before its application to the eye.

Where an indefinite or definite article is used when referring to a singular noun, e.g., "a", "an" or "the", this includes a plural of that noun unless anything else is specifically stated.

Where the term "comprising" is used in the present description and claims, it does not exclude other elements. For the purposes of the present invention, the term "consisting of" is considered to be a preferred embodiment of the term "comprising". If hereinafter a group is defined to comprise at least a certain number of embodiments, this is also to be understood to disclose a group, which preferably consists only of these embodiments.

Terms like "obtainable" or "definable" and "obtained" or "defined" are used interchangeably. This, e.g., means that, unless the context clearly dictates otherwise, the term "obtained" does not mean to indicate that, e.g., an embodiment must be obtained by, e.g., the sequence of steps following the term "obtained" though such a limited understanding is always included by the terms "obtained" or "defined" as a preferred embodiment.

Wherever the terms "including" or "exhibiting" are used, the terms must be considered equivalent to the term "comprising".

According to the present invention, a drop-forming, storage stable, multiphase, ophthalmic composition is provided comprising at least one liquid aqueous phase and at least one liquid hydrophobic phase. The composition is characterized in that it is emulsifier-free as well as buffer-free and comprising hyaluronic acid and/or hyaluronate.

Preferred embodiments of the present invention are described in the following. These embodiments and specifications apply mutatis mutandis to the inventive process and the inventive uses.

The Liquid Aqueous and the Liquid Hydrophobic Phase

The ophthalmic composition of the present invention is multiphasic and comprises at least one liquid aqueous phase and at least one liquid hydrophobic phase. The hydrophobic phase may also be referred to as lipophilic phase.

In one embodiment, the liquid aqueous phase comprises water, and preferably water for injection purposes. In another embodiment, the liquid aqueous phase mimics the natural tear film. By this, the liquid aqueous phase wets the cornea and exerts a cleaning and protective function. In one embodiment, the liquid aqueous phase exhibits a pH value of from 7.1 to 7.8 and/or an osmolality of from 260 to 320 mosmol/kg.

In one embodiment of the present invention, the liquid hydrophobic phase comprises an ophthalmic acceptable oil. In one embodiment of the present invention, the ophthalmic acceptable oil is selected from the group consisting of fatty acid esters, phthalic acid esters, medium-chain triglycerides, long-chain triglycerides, peanut oil, olive oil, coconut oil, sesame oil, cotton seed oil, sunflower oil, corn germ oil, kiwi seed oil, linseed oil, walnut oil, canola oil, chia oil, perilla oil, hemp oil, palm oil, almond oil, fish oil, algae oil, and mixtures thereof.

Preferably, the oil is a biological oil, i.e. an oil of vegetable or animal origin. In one embodiment, the hydrophobic phase comprises an ophthalmic acceptable, vegetable oil, preferably selected from the group consisting of peanut oil, olive oil, coconut oil, sesame oil, cotton seed oil, sunflower oil, corn germ oil, kiwi seed oil, linseed oil, walnut oil, canola oil, chia oil, egoma oil, hemp oil, palm oil, almond oil, and mixtures thereof.

In the meaning of the present invention, "medium-chain triglycerides" exhibit fatty acids with a chain length of from 6 to 12 C atoms. In the meaning of the present invention, "long-chain triglycerides" exhibit fatty acids with a chain length from 14 to 18 C atoms.

In one embodiment, the liquid hydrophobic phase comprises a triglyceride. Suitable triglycerides are available in the form of synthetic, semi-synthetic or natural oils, such as olive oil, palm oil, almond oil, coconut oil, and mixtures thereof. Preferably suitable triglycerides are obtained from coconut oil. Such medium-chain triglycerides are prepared, e.g. from the oil of the endosperm of *Cocus nucifera* L., preferably from the dried part, or from *Elasis guincensis* Jacq. Further preferably suitable triglycerides, preferably medium-chain triglycerides, are neutral oils, e.g. available under the trademark Myritol® 312, Myritol® 318, or Myritol® 331, commercially available from the company Cognis Ltd., Japan. Especially preferred are medium-chain triglycerides as disclosed in the European Pharmacopoeia 5.0, 01/2010:0868, p. 3471, triglycerida saturata media. Preferably, the acid component comprises a mixture with a proportion of n-octanoic acid and n-decanoic acid of at least 90 wt. %, more preferably of at least 94 wt. %, most preferably of at least 95 wt. %, based on the total weight of the fatty acids. Other suitable, medium-chain triglycerides, are commercially available under the trademark Acomed®, Captex®, Neobee® M5F, Miglyol® 810, Miglyol® 812, Mazol® or Sefsol® 860. The medium-chain triglycerides can advantageously prevent the evaporation of the aqueous component and prevent a too fast drying of the tear film or the ophthalmic composition.

In one embodiment, the triglyceride is a medium-chain triglyceride. Based on the total weight of fatty acids, the medium-chain triglyceride can be made up of, e.g. at least 80 wt. %, preferably 90 wt. %, and more preferably 95 wt. % of $C_8$-$C_{12}$ fatty acids, preferably $C_8$-$C_{10}$ fatty acids. Preferably, the medium-chain triglyceride may be a saturated, medium-chain triglyceride. In one embodiment, the saturated medium-chain triglyceride is made up of at least 80 wt. %, preferably at least 90 wt. %, and more preferably at least 95 wt. % of saturated $C_8$-$C_{10}$ fatty acids, based on the total weight of fatty acids.

Especially preferred are caprylic-capric triglycerides, i.e. a mixture made of esterified saturated $C_8$-$C_{10}$ fatty acids. This mixture has the advantage, that the saturated fatty acids can provide an improved stability of the lipid film, and thereby provide a surprisingly improved, longer extension period of the composition in the eye.

In one embodiment, the liquid hydrophobic phase consists of an ophthalmic acceptable oil, preferably selected from the group consisting of fatty acid esters, phthalic acid esters, medium-chain triglycerides, long-chain triglycerides, peanut oil, olive oil, coconut oil, sesame oil, cotton seed oil, sunflower oil, corn germ oil, kiwi seed oil, linseed oil, walnut oil, canola oil, chia oil, perilla oil, hemp oil, palm oil, almond oil, fish oil, algae oil, and mixtures thereof, more preferably selected from the group consisting of fatty acid esters, phthalic acid esters, medium-chain triglycerides, long-chain triglycerides, peanut oil, olive oil, coconut oil, sesame oil, cotton seed oil, sunflower oil, corn germ oil, kiwi seed oil, linseed oil, walnut oil, canola oil, chia oil, perilla oil, hemp oil, palm oil, almond oil, and mixtures thereof, and most preferably the ophthalmic acceptable oil is a medium-chain triglyceride. In another embodiment, the liquid hydrophobic phase comprises an ophthalmic acceptable oil, preferably a triglyceride, and most preferably a medium-chain triglyceride.

In one embodiment, the composition comprises the ophthalmic acceptable oil in an amount of from 0.05 to 10 wt. %, based on the total weight of the composition, preferably from 0.1 to 5 wt. %, more preferably from 0.15 to 2 wt. %, and most preferably from 0.2 to 1.5 wt. %. In a preferred embodiment, the composition comprises the ophthalmic acceptable oil in an amount of less than 0.5 wt. %, based on the total weight of the composition.

Without wishing to be bound by theory, the inventors assume that by adding an ophthalmic acceptable oil, the integrity of the lipid layer of the tear film can be improved or restored, respectively. The inventors of the present invention have found that in the inventive composition already a small amount of ophthalmic acceptable oil provides a suitable evaporation barrier after application to the eye. Thereby, a visual impairment after the application can be prevented or reduced.

In one embodiment, the composition comprises the ophthalmic acceptable oil in an amount of from 0.05 to 0.45 wt. %, based on the total weight of the composition, preferably from 0.1 to 0.4 wt. %, more preferably from 0.15 to 0.35 wt. %, and most preferably from 0.2 to 0.4 wt. %. For example, the inventive composition can comprise the ophthalmic acceptable oil in an amount of from 0.15 to 0.25 wt. %, based on the total weight of the composition.

In one embodiment, the multiphase, ophthalmic composition comprises the liquid aqueous phase as continuous phase, and the liquid hydrophobic phase as droplets dispersed therein. The droplets may have a diameter of from 1 to 30 μm, preferably from 5 to 15 μm.

The preparation is preferably at least two-phasic, and may be three-phasic in preferred embodiments. For example, the composition may comprise an additional aqueous phase with a polymeric, gel-forming component as described further below.

The inventive composition may exhibit a high content of liquid aqueous phase. In one embodiment, the composition comprises the liquid aqueous phase in an amount of from 60 to 99.95 wt. %, based on the total weight of the composition, preferably from 80 to 99.9 wt. %, more preferably from 90 to 99.85 wt. %, and most preferably from 92 to 99.8 wt. %. In another embodiment, the composition comprises the liquid hydrophobic phase in an amount of from 0.05 to 10 wt. %, based on the total weight of the composition, preferably from 0.1 to 5 wt. %, more preferably from 0.15 to 2 wt. %, and most preferably from 0.2 to 1.5 wt. %. In a preferred embodiment, the liquid hydrophobic phase fully consists of the ophthalmic acceptable oil.

Hyaluronic Acid and/or Hyaluronate

The ophthalmic composition of the present invention is characterized in that it comprises hyaluronic acid and/or hyaluronate.

Hyaluronic acid is a naturally occurring, highly viscous glycosaminoglycan consisting of the glucose derivatives D-glucuronic acid and N-acetyl-D-glucosamine. Depending on the extraction procedure, the molecular weight $M_w$ of the hyaluronic acid can range from 50 000 to 10 000 000 g/mol. The hyaluronic acid is a component of the extracellular matrix of vertebrates and specifically a natural component of the human eye fluid. The hyaluronic acid may be obtained from animal or vegetable sources or may be prepared synthetically or semi-synthetically.

In one embodiment of the present invention, the composition comprises hyaluronic acid and/or hyaluronate in an amount of at least 0.001 wt. %, based on the total weight of the composition, preferably in an amount of at least 0.01 wt. %, more preferably in an amount of at least 0.1 wt. %, even more preferably in an amount of at least 0.15 wt. % and most preferably in an amount of at least 0.2 wt. %. In another embodiment of the present invention, the composition comprises hyaluronic acid and/or hyaluronate in an amount of from 0.001 to 5 wt. %, based on the total weight of the composition, preferably in an amount of from 0.01 to 2 wt. %, more preferably in an amount of from 0.1 to 1.5 wt. %, even more preferably in an amount of from 0.15 to 1 wt. %, and most preferably in an amount of from 0.2 to 0.8 wt. %. For example, the inventive composition can comprise hyaluronic acid and/or hyaluronate in an amount of from 0.15 to 0.3 wt. %, based on the total weight of the composition.

In one embodiment, the molecular weight $M_w$ of the hyaluronic acid and/or hyaluronate ranges from 50 000 to 10 000 000 g/mol, preferably from 100 000 to 5 000 000 g/mol, and most preferably from 250 000 to 1 000 000 g/mol.

Instead of the free hyaluronic acid or additionally to the free hyaluronic acid, also a salt of the hyaluronic acid, i.e. a hyaluronate, may be employed in the ophthalmic composition of the present invention. In one embodiment, the hyaluronate is selected from the group consisting of sodium hyaluronate, potassium hyaluronate, zinc hyaluronate and mixtures thereof. In a preferred embodiment, the hyaluronate is sodium hyaluronate.

The inventors of the present invention have surprisingly found that hyaluronic acid and/or hyaluronate improves the stability, and particularly the storage stability, of multiphasic ophthalmic compositions. Without wishing to be bound by theory, the inventors assume that the hyaluronic acid and/or the hyaluronate stabilize the droplets of the liquid hydrophobic phase dispersed in the liquid aqueous phase by a sterical effect.

Furthermore, it was surprisingly found that the inventive composition remains stable over a longer period of time also in lower viscosity ranges, particularly at a viscosity of less than 350 mPa·s, for example, less than 250 mPa·s or less than 200 mPa·s. This is particularly advantageous for the composition of low viscosity emulsions, since they typically become instable upon storage and demix. It is of particular advantage that a composition with a low viscosity improves significantly the applicability for the patient. Thereby, a drop-forming composition advantageously can be provided that, due to its low viscosity, can be distributed better on the cornea of the eye, and the eye has not to be irritated by an additional mechanical support of the distribution. Furthermore, it is advantageous that a composition with low viscosity causes only little sensation of foreign matter in the eye upon application and provides a more pleasant tolerance for the patient. Moreover, compositions with low viscosity are easier to administer from a dosing container and are easier to apply. It is also possible to provide compositions with low viscosity in form of eye lid sprays, which are also easier to administer for a patient.

A particular advantage of the inventive composition is that the stability of the ophthalmic composition is achieved without addition of emulsifiers. Furthermore, the addition of a buffer is not necessary. Thereby, according to the invention an emulsifier-free and buffer-free composition can be provided. This allows an improvement of the tolerance of the inventive composition and avoids irritation or "burning" of the eye.

According to one aspect of the present invention, use of hyaluronic acid and/or hyaluronate is provided for the stabilization of a multiphase, emulsifier-free composition comprising at least one liquid aqueous phase and at least one liquid hydrophobic phase. In one embodiment of the present invention, use of hyaluronic acid and/or hyaluronate is provided for the stabilization of a drop-forming, multiphase, emulsifier-free, buffer-free composition comprising at least one liquid aqueous phase and at least one liquid hydrophobic phase.

Further Components

In addition to the above-described components, the ophthalmic composition of the present invention can comprise further components.

In one embodiment, the composition comprises at least one polymeric, gel-forming component. Thereby, for example, the viscosity of the composition can be specifically controlled. Moreover, the adsorbability of the composition to the mucin layer of the tear film can be improved by a polymeric, gel-forming component, and thereby the retention period of the composition in the eye is prolonged. The lubricating properties and/or the water binding ability of the composition can also be improved by the presence of a polymeric, gel-forming component.

Preferably the polymeric, gel-forming component comprises at least one polyacrylic acid and/or at least one polymeric acrylic acid derivative.

Preferred polyacrylic acids or polymeric acrylic acid derivatives exhibit a molecular weight $M_w$ in the range of from about 3 to 5 million g/mol. Particularly preferred, applicable polyacrylic acids or polymeric acrylic acid derivatives are those cross-linked acrylic acid polymers, preferably hydrophobically modified cross-linked acrylic acid polymers, described as carbomer under the INCI description. Preferred carbomers are available under the trademark Carbopol®, for example, from the company The Lubrizol Corporation U.S.A. Particularly preferred carbomers are acrylic acid-homopolymers, for example, Carbopol®-homopolymers, particularly preferred is Carbopol® 980 NF, further particularly preferred is Carbopol® 940 NF. The terms polyacrylic acid and polymeric acrylic acid are used interchangeably for the purpose of the present application. According to a preferred embodiment, the inventive composition comprises at least one carbomer.

In one embodiment, the composition comprises the polymeric, gel-forming component in an amount of from 0.01 to 5 wt. %, based on the total weight of the composition, preferably from 0.02 to 3 wt. %, more preferably from 0.04 to 1 wt. %, and most preferably from 0.05 to 0.08 wt. %. In another embodiment, the composition comprises at least one polyacrylic acid and/or polymeric acrylic acid, preferably at least one carbomer, in an amount of from 0.01 to 5 wt. %, based on the total weight of the composition, preferably from 0.02 to 3 wt. %, more preferably from 0.04 to 1 wt. %, and most preferably from 0.05 to 0.1 wt. %.

In one embodiment, the composition comprises the polymeric, gel-forming component in an amount such that the composition exhibits a viscosity of less than 350 mPa·s at 20° C., preferably less than 250 mPa·s at 20° C., more preferably less than 200 mPa·s at 20° C., and even more preferably less 150 mPa·s at 20° C., and most preferably less than 100 mPa·s at 20° C.

In one embodiment, the inventive composition comprises an agent to adjust the isotonicity, i.e. an isotonizing agent. Non-electrolytes and/or electrolytes are suitable isotonizing agents. Examples of suitable non-electrolytes to adjust the isotonicity are dextrose, glycerin, propylene glycol, sorbitol, mannitol, urea, polyethylene glycol and mixtures thereof. Examples of suitable electrolytes to adjust the isotonicity are boric acid, magnesium sulfate, zinc sulfate, sodium chloride, potassium chloride, calcium chloride, sodium sulfate, sodium hydrogen phosphate, trisodium citrate, trisodium phosphate, and mixtures thereof.

In one embodiment, the composition comprises an agent to adjust the isotonicity selected from the group consisting of dextrose, glycerin, propylene glycol, sorbitol, mannitol, urea, polyethylene glycol, boric acid, magnesium sulfate, zinc sulfate, sodium chloride, potassium chloride, calcium chloride, sodium sulfate, sodium hydrogen phosphate, trisodium citrate, trisodium phosphate, and mixtures thereof, preferably selected from the group consisting of dextrose, glycerin, propylene glycol, sorbitol, mannitol, urea, polyethylene glycol, and mixtures thereof. In a preferred embodiment, the agent to adjust the isotonicity is glycerin.

In one embodiment, the composition comprises the agent to adjust the isotonicity in an amount that is sufficient to provide the composition isotonically to natural tear fluid. In a preferred embodiment, the composition comprises the agent to adjust the isotonicity in an amount of from 0.1 to 10 wt. %, based on the total weight of the composition, preferably from 0.5 to 9 wt. %, more preferably from 1 to 8 wt. %, and most preferably from 1.5 to 7 wt. %. In another preferred embodiment, the composition comprises glycerin as isotonizing agent in an amount of from 0.1 to 10 wt. %, based on the total weight of the composition, preferably from 0.5 to 9 wt. %, more preferably from 1 to 5 wt. %, and most preferably from 2 to 3 wt. %. In one embodiment the composition comprises the agent to adjust the isotonicity in an amount such that the composition exhibits an osmolality of from 100 to 500 mosmol/kg, preferably from 200 to 400 mosmol/kg, and most preferably from 260 to 320 mosmol/kg.

The inventive composition preferably does not contain any pharmaceutical substances or active pharmaceutical ingredients such as anti-viral agents, steroidal or non-steroidal anti-inflammatory compounds or corticosteroids, antibiotics, antimycotics, narcotics, anti-inflammatory agents or anti-allergic agents. "Active pharmaceutical ingredients", for the purpose of the invention, are particularly not vitamin A and vitamin E.

In one embodiment, the inventive composition comprises at least one ophthalmic active ingredient. For example, the inventive composition may contain pharmaceutical substances or active pharmaceutical ingredients such as anti-viral agents, steroidal and non-steroidal anti-inflammatory compounds or corticosteroid, antibiotics, antimycotics, narcotics, anti-inflammatory agents, immunosuppressive agents and/or anti-allergic agents.

In one embodiment, the composition additionally comprises an immunosuppressive agent, preferably selected from the group of cyclosporine A, azathioprine, cyclophosphamide, tacrolimus hydrate, mycophenolate-mofetil, mycophenolic acid, pimecrolimus, pimecrolimus hydrate, sirolimus, sirolimus hydrate, and mixtures thereof. In a preferred embodiment, the composition additionally comprises cyclosporine A.

In a further embodiment, the composition additionally comprises a vitamin A component, preferably vitamin A palmitate.

In one embodiment, the composition comprises at least one ophthalmic active ingredient, preferably a vitamin A component, most preferably vitamin A palmitate, and/or an antioxidant, most preferably vitamin E. The amount of vitamin A palmitate preferably can be 1000 I.U. vitamin A palmitate per gram of composition, whereby preferably an additional 20% extra stability amount is used. Preferably suitable vitamin A palmitate has 1 million I.U. per gram of vitamin A palmitate, and preferably comprises butylated hydroxyanisole and/or butylated hydroxytoluene as stabilisers. In one embodiment, the composition comprises a vitamin A component, particularly vitamin A palmitate, in an amount of from 0.05 to 0.5 wt. %, preferably from 0.08 to 0.2 wt. %, and most preferably in an amount of about 0.1 wt.

%, with consideration of the extra stability amount of about 0.12 wt. %, based on the total weight of the composition.

Particularly preferred, the vitamin A component is used in combination with an antioxidant such as vitamin E. The vitamin A component may be stabilized with at least one antioxidant, preferably vitamin E, more preferably D,L-α-tocopherol. For the stabilization, a small amount of the antioxidant, preferably vitamin E, more preferably D,L-α-tocopherol, is used, for example, in an amount of from 0.002 to 0.01 wt. %, preferably from 0.006 to 0.008 wt. %, based on the total weight of the composition.

Another advantage of the inventive composition is that a suspended or in the liquid hydrophobic phase dissolved active ingredient can be more evenly distributed. Thereby, the wettability of objects that can be placed on the cornea, such as contact shells or front lenses of ophthalmic devices, can be improved.

The pH value of the inventive composition can be adjusted with acids and/or bases. For example, the pH value may be adjusted with boric acid and/or sodium hydroxide solution. In one embodiment, the inventive composition comprises an acid and/or a base in an amount of from 0.01 to 1 wt. %, based on the total weight of the composition, preferably from 0.02 to 0.5 wt. %, and most preferably from 0.02 to 0.05 wt. %6.

In one embodiment, the composition comprises sodium hydroxide solution for the adjustment of the pH value. For the adjustment of the pH value, a solution of 2% to 3% sodium hydroxide is particularly suitable. In one embodiment, the inventive composition comprises sodium hydroxide in an amount of from 0.01 to 1 wt. %, based on the total weight of the composition, preferably from 0.02 to 0.5 wt. %, and most preferably from 0.02 to 0.05 wt. %.

Furthermore, the inventive composition may comprise a water-soluble phosphate salt.

In a preferred embodiment of the present invention the composition is free of phosphate salts.

In one embodiment, the inventive composition exhibits a pH value in the range of from 6 to 8, preferably in the range of from 6.5 to 7.5, and most preferably in the range of from 6.8 to 7.2. According to an exemplary embodiment, the inventive composition exhibits a pH value in the range of from 6 to 7.

The inventive composition may comprise further components, for example preservatives, preferably selected from the group of cetrimide, benzododecinium chloride, benzalkonium chloride, thiomersal, alexidine, and mixtures thereof, and most preferably cetrimide, and/or alexidine. "Cetrimide" is a common name for N-cetyl-N,N,N-trimethyl-ammonium bromide, "benzododecinium chloride" for N-benzyl-N-dodecyl-N,N-dimethyl-ammonium chloride, "benzalkonium chloride" for benzyllauryldimethylammonium chloride, and "thiomersal" for the sodium salt of 2-(ethylmercurithio)benzoic acid sodium salt. For the purpose of the invention, alexidine does not relate to an emulsifier, or the amount of alexidine used, does not exhibit an emulsifying effect.

In one embodiment, the inventive composition comprises a preservative in an amount of from 0.001 to 0.05 wt. %, based on the total amount of the composition, preferably from 0.005 to 0.01 wt. %.

In a particularly preferred embodiment, the inventive composition is free of preservatives.

In one embodiment of the present invention, the drop-forming, storage stable, multiphase, ophthalmic composition comprises hyaluronic acid and/or a hyaluronate, an ophthalmic acceptable oil, at least one polymeric, gel-forming component, an agent to adjust the isotonicity, a base and water. In a further embodiment of the present invention, the drop-forming, storage stable, multiphase, ophthalmic composition comprises hyaluronic acid and/or a hyaluronate, preferably a hyaluronate, a medium-chain triglyceride, at least one polyacrylic acid and or at least one polymeric polyacrylic acid derivative, an agent to adjust the isotonicity, a base and water. In a further embodiment of the present invention, the drop-forming, storage stable, multiphase, ophthalmic composition comprises hyaluronic acid and/or a hyaluronate, a medium-chain triglyceride, a carbomer, an agent to adjust the isotonicity selected from the group consisting of dextrose, glycerin, propylene glycol, sorbitol, mannitol, urea, polyethylene glycol, and mixtures thereof, a base, preferably sodium hydroxide, and water. In one embodiment, the inventive composition is free of phosphate salts and preservatives.

In one embodiment of the present invention, the drop-forming, storage stable, multiphase, ophthalmic composition comprises the following substances, based on the total weight of the composition:

Hyaluronic acid and/or a hyaluronate, preferably a hyaluronate, in an amount of from 0.001 to 5 wt. %, preferably from 0.01 to 2 wt. %, more preferably from 0.1 to 1.5 wt. %, even more preferably from 0.15 to 1 wt. %, and most preferably from 0.2 to 0.8 wt. %, an ophthalmic acceptable oil, preferably a medium-chain triglyceride, in an amount of from 0.05 to 10 wt. %, preferably from 0.1 to 5 wt. %, more preferably from 0.15 to 2 wt. %, and most preferably from 0.2 to 1.5 wt. %, at least one polymeric gel-forming component, preferably a polyacrylic acid and/or a polymeric polyacrylic acid derivative, more preferably a carbomer, in an amount of from 0.01 from 5 wt. %, preferably from 0.02 to 3 wt. %, more preferably from 0.04 to 1 wt. %, and most preferably from 0.05 to 0.1 wt. %, an agent to adjust the isotonicity selected from the group of dextrose, glycerin, propylene glycol, sorbitol, mannitol, urea, polyethylene glycol, and mixtures thereof, preferably glycerin, in an amount of from 0.1 to 10 wt. %, preferably from 0.5 to 9 wt. %, more preferably from 1 to 8 wt. %6, and most preferably from 1.5 to 7 wt. %, a base, preferably sodium hydroxide, in an amount of from 0.01 to 1 wt. %, based on the total weight of the composition, preferably from 0.02 to 0.5 wt. %, and most preferably from 0.02 to 0.05 wt. %, and water.

In one embodiment the drop-forming, storage stable, multiphase, ophthalmic composition comprises the following substances, based on the total weight of the composition:
  0.15 to 0.3 wt. % sodium hyaluronate,
  0.15 to 0.25 wt. % medium-chain triglycerides,
  0.05 to 0.1 wt. % carbomer,
  1.5 to 7 wt. % agents to adjust the isotonicity, preferably glycerin, sodium hydroxide for pH adjustment, preferably in an amount of from 0.02 to 0.05 wt. %, and
  q.s. ad 100 wt. % water.

The expression "q.s. ad 100 wt. % water" means, for the purpose of the present invention, that water is added in such an amount, to reach a total amount of 100 wt. %.

In a preferred embodiment, the inventive composition does not contain further substances besides the ones mentioned above.

Properties, Preparation and Use

According to the present invention, a drop-forming, storage stable, multiphase, ophthalmic composition is provided comprising at least one liquid aqueous phase and at least one liquid hydrophobic phase characterized in that the composition is emulsifier-free, the composition is buffer-free, and the composition comprises hyaluronic acid and/or hyaluronate.

The inventive composition can be provided in any suitable liquid formulation known to the skilled person. According to one embodiment the composition is in form of an eye lid spray, an eye bath, an eye wash solution, or eye drops. According to a preferred embodiment the composition is in form of an eye lid spray or eye drops.

In one embodiment, the composition exhibits a viscosity of less than 350 mPa·s at 20° C., preferably less than 250 mPa·s at 20° C. more preferably less than 200 mPa·s at 20° C., and even more preferably less 150 mPa·s at 20° C., and most preferably less than 100 mPa·s at 20° C. According to the present invention, the viscosity is determined by the Wells-Brookfield cone and plate procedure with a Wells-Brookfield cone and plate viscometer of the type DV-III+ (Brookfield Engineering Laboratories GmbH, Germany) equipped with a CP51 spindle at 5 rpm and 20° C.

The inventive composition is prepared aseptically without difficulties and is well tolerated. Suitable processes for the preparation of multiphase compositions are known to the person skilled in the art. The preparation of the inventive composition preferably takes place in a multistep process. In particular, hyaluronic acid and/or hyaluronate is added to the liquid aqueous phase of the inventive composition. It will be appreciated that the ophthalmic composition is provided in a sterile form for use, that sterile substances are applied under sterile conditions, or that the composition is sterilized after addition of the substances.

According to another aspect of the present invention, a process for the preparation of a drop-forming, storage stable, multiphase, ophthalmic composition is provided comprising at least one liquid aqueous phase and at least one liquid hydrophobic phase, characterized in that a liquid hydrophobic phase is dispersed homogeneously in a continuous liquid aqueous phase, wherein the liquid aqueous phase comprises hyaluronic acid and/or hyaluronate.

In a preferred process for the preparation of the inventive composition, hyaluronic acid and/or hyaluronate is first dissolved in the liquid aqueous phase, preferably under aseptic conditions. The hydrophobic liquid phase is then dispersed in this liquid aqueous phase, preferably under aseptic conditions. Preferably, it is stirred until complete homogenization. The diameter of the thus obtained droplets of the hydrophobic liquid phase in the dispersion is preferably less than 100 μm. In a preferred embodiment, it is homogenized until droplets of a diameter of from 1 to 30 μm, preferably from 5 to 15 μm, are obtained. Afterwards, the obtained, preferably sterile, composition can be packaged in a standard manner.

In another embodiment, a polymeric, gel-forming component is added to the liquid aqueous phase. Thereby, a three-phase composition can be provided which comprises a gel phase or mucin phase, respectively, in addition to the liquid aqueous phase and the liquid hydrophobic phase. Furthermore, an isotonizing agent and/or further above-described components may be added to the liquid aqueous phase.

In an exemplary embodiment, a suspension of at least one polyacrylic acid and/or at least one acrylic acid derivative is prepared first, preferably under aseptic conditions. An aqueous sterile-filtered solution that comprises hyaluronic acid and/or hyaluronate as well as, if necessary, an isotonizing agent, is subsequently added to this suspension, whereby it may be worked under application of, preferably sterile-filtered, nitrogen or compressed air as compressed gas. After thoroughly mixing, the carboxylic groups of the at least one polyacrylic acid and/or at least one acrylic acid derivative are neutralized by addition of a, preferably sterile, 2% to 3% solution of sodium hydroxide, the gel formation of the at least one polyacrylic acid and/or at least one acrylic acid derivative is initiated and the mixture is preferably stirred until homogeneity of the gel is achieved. The liquid hydrophobic phase is then added to the prepared hydrogel under aseptic conditions.

Furthermore, an ophthalmic active ingredient, e.g. vitamin A palmitate, may be added to the thus obtained, sterile gel. In an exemplary embodiment, the active ingredient is added under aseptic conditions and homogeneously mixed thereto. For example, a vitamin A component and the present, preferably much lower, amount of an antioxidant may be dissolved in the hydrophobic phase and then filtered sterilely. The sterile hydrophobic active ingredient-containing phase may then be added to the gel under stirring.

The inventive composition is particularly suitable for treating diseases or conditions of the eye, or of the organs or tissue surrounding the eye or connected therewith. The ophthalmic composition is particularly suitable relieving discomfort related to dry eye and/or for symptomatic treatment of the dry eye.

According to another aspect of the present invention, a drop-forming, storage stable, multiphase, ophthalmic composition for use as a medicament is provided, whereby the composition comprises at least one liquid aqueous phase and at least one liquid hydrophobic phase and is characterized in that it is emulsifier-free and buffer-free, and comprises hyaluronic acid and/or hyaluronate. In one embodiment, a drop-forming, storage stable, multiphase, ophthalmic composition, according to the present invention, for use in treating diseases or condition of the eye, or the organs or tissues surrounding the eye or being connected therewith, and preferably for use in treating dry eye, whereby the composition comprises at least one liquid aqueous phase and at least one liquid hydrophobic phase and is characterized in that it is emulsifier-free and buffer-free, and comprises hyaluronic acid and/or hyaluronate.

Due to the absence of eye-irritating substances, e.g. emulsifiers or buffer substances, the inventive ophthalmic composition is suited for long-term treatment of dry eye, for example, as a tear replacement agent. Surprisingly, it was found that already within a few minutes after the application of the inventive composition a significant improvement of the disorders such as feeling of dryness at the eye, but also burning, itching, redness or swelling, can be achieved. It is of particular advantage that the disorders are alleviated by the inventive composition for a long time. The preservative-free and/or phosphate-free inventive composition is especially suited for a long-term treatment.

For the application, the inventive composition may be filled in suitable container, that are preferably designed such that the content may be applied to the eye.

According to another aspect, a container comprising the composition of the present invention is provided, whereby the container is a single-dose container or multi-dose container preferably an ophtiole, a single-dose ophtiole or an application system, preferably a pump-based application system or a tip-seal application system.

In one embodiment of the present invention, the inventive composition is provided in a type of a single-dose container. Single-dose containers are known in the prior art, for example, under the designation single-dose Ophtiole®, and may preferably be made of polyethylene such as LDPE (low density polyethylene). In a particularly preferred embodiment, the inventive composition is provided in a single-dose container free from preservatives.

Alternatively, the container which comprises the inventive composition, may also be a multi-dose container. For example, the container may be a dropping bottle. Suitable dropping bottles are known in the prior art, e.g. under the designation Ophtiole®, and may be made from polyethylene, preferably HDPE (high density polyethylene) or LDPE (low density polyethylene).

The multi-dose container may also be an application system such as a pump-based application system or a tip-seal system. Examples for pump-based application systems are eye lid sprays, dosage spray bottles, or eye dropping pumps such as the COMOD® system or the 3K® system, both produced by the company Ursatec Verpackung GmbH. Examples for the tip-seal system are the Ophthalmic Squeeze Dispenser (OSD®) system from the company Aptargroup, Inc., or the Novelia® system from the company Nemera.

According to one embodiment a dosage spray bottle comprising a composition of the present invention, wherein preferably the composition is in form of an eye lid spray. Thereby, the eye lid spray can be applied to the eye in form of a spray mist. Typically, eye lid sprays are sprayed onto the closed eye lid several times a day. However, it is also possible to apply the inventive eye lid spray from the front or from the side to the open eye. Once the inventive composition gets into contact with the tear film of the eye, the viscosity of the composition may be reduced due to the salt content of the tear film, thereby destabilizing the composition. As a result, the liquid aqueous and the liquid hydrophobic phase may separate and a homogeneous hydrophobic film, e.g. an oil film, can be formed on the tear film of the eye, thereby providing an evaporation barrier and/or improving or restoring the integrity of the lipid layer. Thus, a fast, direct, and effective action can be provided.

This is an advantage compared to the liposomal eye lid sprays known in the art, which typically include phospholipid-containing liposomes. The lipids contained in the liposomes should be integrated into the lipid layer of the tear film, thereby stabilizing the same, which seems to require a break-up of the liposomes. Furthermore, liposomal eye lid sprays often have an inherent odor, which is experienced as unpleasant by the patients.

Scope and subject-matter of the present invention will be illustrated by the following examples based on selected embodiments, that shall not be understood as limitations or restrictions.

EXAMPLES

1. Measuring Methods pH Value

The pH value of the prepared, ophthalmic composition was measured at a temperature of 20° C. with a Knick pH-Meter 765 or Knick pH-Meter 766 (Knick Elektronische Messgeräte GmbH & Co. KG, Germany).

Osmolality

The osmolality of the prepared, ophthalmic composition was measured at a temperature of 20° C. with a micro osmometer (Hermann Röbling Messtechnik, Germany).

Viscosity

The viscosity of the prepared, ophthalmic composition was determined by the Wells-Brookfield cone and plate procedure with a Wells-Brookfield cone and plate viscometer of the type DV-III+ (Brookfield Engineering Laboratories GmbH, Germany) equipped with a CP51 spindle at 5 rpm and 20° C.

Measurement of Droplet Size

The diameter of the droplets of the liquid hydrophobic phase was determined microscopically with the microscope Axio Imager M1 (Carl Zeiss AG, Germany).

Dropping Experiment (Priming)

The dropping experiments were performed manually by perpendicular operation of a pump-based application system (3K® system, Ursatec Verpackung GmbH, Germany). The required operations were determined for the release of a drop of medium drop size by the application system.

Stability Test

The storage stability of the prepared, ophthalmic composition was determined by centrifugation of the composition at a speed of 5700 rounds per minute at 20° C. over a period of 60 minutes. A laboratory centrifuge Multifuge 1 S (Kendro Laboratory Products GmbH, Germany) was used for the investigation.

After completion of the centrifugation the composition was examined visually and was evaluated as follows:

OK: No optical separation or differences in turbidity visible

ET: Turbidity visible from below

2. Substances

HA: Sodium hyaluronate (Bloomage Freda Biopharm Co., Ltd., China).

MCT: Caprylic-capric acid triglyceride (Myritol 318, BASF AG, Germany).

Carbomer: Carbopol 980 NF (Lubrizol Advanced Materials Europe BVBA, Belgium).

IM: Isotonizing agent; the following substances were employed: Glycerin, sorbitol, mannitol, glucose, propylene glycol, urea, PEG 300.

3. Example

Ophthalmic compositions labeled with sample 1 to 9 were prepared according to the following process by using the substances and quantities listed in Table 1.

In the first step of the preparation, carbomer was suspended in water and subsequently autoclaved. In the second step, a sterile aqueous solution comprising water, sodium hyaluronate and an isotonizing agent was prepared and added to the carbomer suspension. Thereafter, a pH value of 6 to 7 was adjusted, if necessary, by adding a sterile sodium hydroxide solution, and the liquid hydrophobic phase was added under homogenization. The final composition was aseptically filled in a primary package.

The results summarized in Table 2 show that all inventive samples 2 to 9 pass the stability test and therefore are storage stable. In contrast, the comparative sample 1 without hyaluronate shows after performance of the stability test a turbidity visible from below, which indicates a demixing of the phases.

TABLE 1

Substances and quantities of the prepared samples 1 to 9 (Comp.: Comparative sample).

| Substance | Sample 1 (Comp.) | Sample 2 | Sample 3 | Sample 4 | Sample 5 | Sample 6 | Sample 7 | Sample 8 | Sample 9 |
|---|---|---|---|---|---|---|---|---|---|
| HA [mg/g] | — | 2.4 | 2.4 | 2.4 | 2.4 | 2.4 | 2.4 | 2.4 | 1.7 |
| MCT [mg/g] | 2.0 | 2.0 | 2.0 | 2.0 | 2.0 | 2.0 | 2.0 | 2.0 | 2.0 |
| Carbomer [mg/g] | 0.625 | 0.625 | 0.625 | 0.625 | 0.625 | 0.625 | 0.625 | 0.625 | 0.625 |
| NaOH | q.s. pH 6-7 | q.s. pH 6-7 | q.s. pH 6-7 | q.s. pH 6-7 | q.s. pH 6-7 | q.s. pH 6-7 | q.s. pH 6-7 | q.s. pH 6-7 | q.s. pH 6-7 |
| IM [mg/g] | Glycerin 29.0 | Glycerin 29.0 | Sorbitol 50.0 | Mannitol 49.0 | Glucose 52.8 | Propylene glycol 20.0 | Urea 16.3 | PEG 300 65.0 | Glycerin 29.0 |
| Water | ad 1 g | ad 1 g | ad 1 g | ad 1 g | ad 1 g | ad 1 g | ad 1 g | ad 1 g | ad 1 g |

TABLE 2

Properties of the prepared samples 1 to 9 (Comp.: Comparative sample).

|  | Sample 1 (Comp.) | Sample 2 | Sample 3 | Sample 4 | Sample 5 | Sample 6 | Sample 7 | Sample 8 | Sample 9 |
|---|---|---|---|---|---|---|---|---|---|
| pH value | 7.3 | 7.1 | 7.1 | 7.1 | 7.2 | 7.3 | 7.1 | 7.7 | 7.0 |
| Osmolality [mosmol/kg] | 287 | 269 | 294 | 283 | 286 | 270 | 271 | 274 | 287 |
| Viscosity [μm] | 123 | 202 | 209 | 194 | 183 | 184 | 174 | 199 | 166 |
| Size of droplet [μm] | 9-12 | 9-11 | 11-12 | 7-10 | 8-11 | 9-10 | 8-10 | 9-11 | 5-10 |
| Dropping test (priming) | 8 | 10 | 10 | 18 | 18 | 10 | 15 | 10 | 10 |
| Stability test | ET | OK | OK | OK | OK | OK | OK | OK | OK |

The invention claimed is:

1. A storage stable, multiphase, ophthalmic composition comprising at least one liquid aqueous phase and at least one liquid hydrophobic phase, characterized in that:
    the composition is emulsifier-free;
    the composition is buffer-free;
    the composition is free of a phosphate salt;
    the composition exhibits a viscosity of less than 250 mPa·s at 20° C.;
    wherein the at least one liquid aqueous phase comprises water and exhibits one or more of a pH value of from 6 to 8 and an osmolality of from 200 to 400 mosmol/kg, and the at least one liquid hydrophobic phase comprises an ophthalmic acceptable oil; and
    wherein the composition comprises hyaluronic acid and/or hyaluronate, characterized in that the hyaluronic acid and/or hyaluronate exhibits a molecular weight $M_w$ of from 50,000 to 1,000,000 g/mol.

2. The composition according to claim 1, characterized in that the composition comprises hyaluronic acid and/or hyaluronate in an amount of at least 0.001 wt. % to 5 wt. %, based on the total weight of the composition.

3. The composition according to claim 1, characterized in that the hyaluronate is selected from the group consisting of sodium hyaluronate, potassium hyaluronate, zinc hyaluronate, and mixtures thereof.

4. The composition according to claim 1, characterized in that the composition comprises the liquid aqueous phase as a continuous phase, and the liquid hydrophobic phase as droplets dispersed therein.

5. The composition according to claim 1, characterized in that the composition further comprises at least one polymeric gel-forming component.

6. The composition according to claim 5, wherein the at least one polymeric gel-forming component comprises at least one of a polyacrylic acid and a polymeric polyacrylic acid derivative.

7. The composition according to claim 1, wherein the ophthalmic acceptable oil is a triglyceride.

8. The composition according to claim 1, characterized in that the composition further comprises an isotonicity agent.

9. The composition according to claim 8, wherein the isotonicity agent is selected from the group consisting of dextrose, glycerin, propylene glycol, sorbitol, mannitol, urea, polyethylene glycol, boric acid, magnesium sulfate, zinc sulfate, sodium chloride, potassium chloride, calcium chloride, sodium sulfate, and mixtures thereof.

10. The composition according to claim 1, wherein the at least one liquid aqueous phase exhibits a pH value of from 7.1 to 7.8 and an osmolality of from 260 to 320 mosmol/kg.

11. The composition according to claim 10, characterized in that the composition comprises the ophthalmic acceptable oil in an amount of from 0.05 to 10 wt. %, based on the total weight of the composition.

12. The composition according to claim 1, characterized in that the composition comprises:
    0.15 to 0.3 wt. %, based on the total weight of the composition, of sodium hyaluronate,
    0.15 to 0.25 wt. %, based on the total weight of the composition, of a medium-chain triglyceride,
    0.05 to 0.1 wt. %, based on the total weight of the composition, of a carbomer,
    1.5 to 7 wt. %, based on the total weight of the composition, of an isotonicity agent,
    sodium hydroxide for pH adjustment, and
    q.s. ad 100 wt. % water.

13. The composition according to claim 1, characterized in that the composition is in form of an eye lid spray, an eye bath, an eye wash solution, or eye drops.

14. A container comprising a drop-forming, storage stable, multiphase, ophthalmic composition, wherein the container is a single-dose container or a multi-dose container; wherein the drop-forming, storage stable, multiphase, ophthalmic composition comprises at least one liquid aqueous phase and at least one liquid hydrophobic phase, characterized in that:

the composition is emulsifier-free;
the composition is buffer-free;
the composition is free of a phosphate salt;
the composition exhibits a viscosity of less than 250 mPa·s at 20° C.;
wherein the at least one liquid aqueous phase comprises water and exhibits one or more of a pH value of from 7.1 to 7.8 and an osmolality of from 260 to 320 mosmol/kg, and the at least one liquid hydrophobic phase comprises an ophthalmic acceptable oil; and
wherein the composition comprises hyaluronic acid and/or hyaluronate, characterized in that the hyaluronic acid and/or hyaluronate exhibits a molecular weight $M_w$ of from 50,000 to 1,000,000 g/mol.

15. The container according to claim 14, wherein the composition comprises:
   0.15 to 0.3 wt. %, based on the total weight of the composition, of sodium hyaluronate,
   0.15 to 0.25 wt. %, based on the total weight of the composition, of a medium-chain triglyceride,
   0.05 to 0.1 wt. %, based on the total weight of the composition, of a carbomer,
   1.5 to 7 wt. %, based on the total weight of the composition, of an isotonicity agent,
   sodium hydroxide for pH adjustment, and
   q.s. ad 100 wt. % water.

16. The composition according to claim 1, wherein the hyaluronic acid and/or hyaluronate is present in the composition in an amount of 0.15 to 0.3 wt. %, based on the total weight of the composition.

17. The composition according to claim 1, exhibiting a viscosity of less than 200 mPa·s at 20° C.

18. The container according to claim 14, wherein the composition comprises 0.15 to 0.3 wt. %, based on the total weight of the composition, of hyaluronic acid and/or hyaluronate.

19. The container according to claim 14, characterized in that the composition further comprises at least one polymeric gel-forming component.

20. The container according to claim 19, wherein the at least one polymeric gel-forming component comprises at least one of a polyacrylic acid and a polymeric polyacrylic acid derivative.

* * * * *